US012766271B2

(12) United States Patent
Hibbetts

(10) Patent No.: US 12,766,271 B2
(45) Date of Patent: Oct. 20, 2026

(54) TOPICAL ANESTHETIZING APPARATUS

(71) Applicant: Shane S Hibbetts, Yucaipa, CA (US)

(72) Inventor: Shane S Hibbetts, Yucaipa, CA (US)

( * ) Notice: Subject to any disclaimer, the term of this patent is extended or adjusted under 35 U.S.C. 154(b) by 860 days.

(21) Appl. No.: 18/120,331

(22) Filed: Mar. 10, 2023

(65) Prior Publication Data

US 2024/0299673 A1 Sep. 12, 2024

(51) Int. Cl.

*A61M 5/42* (2006.01)

*A61H 15/00* (2006.01)

(52) U.S. Cl.

CPC ..... *A61M 5/422* (2013.01); *A61H 2015/0064* (2013.01); *A61H 15/0092* (2013.01)

(58) Field of Classification Search

CPC ............... A61M 5/422; A61H 15/0085; A61H 2015/0042; A61H 2015/0065; A61H 2015/0064

See application file for complete search history.

(56) References Cited

U.S. PATENT DOCUMENTS

| | | | | |
|---|---|---|---|---|
| 4,082,089 | A * | 4/1978 | Moriyama | A61N 2/002 601/19 |
| D1,003,731 | S * | 11/2023 | Fufidio | D9/420 |
| 2002/0173738 | A1 * | 11/2002 | Rogalski | A61F 13/108 602/20 |
| 2006/0155225 | A1 * | 7/2006 | Murdock | A61H 15/02 601/119 |
| 2016/0279017 | A1 * | 9/2016 | Hyder | A61H 15/00 |
| 2018/0161235 | A1 * | 6/2018 | Chen | A61H 15/02 |
| 2019/0167915 | A1 * | 6/2019 | Gildea | A61M 5/422 |

* cited by examiner

*Primary Examiner* — James D Ponton

(74) *Attorney, Agent, or Firm* — Cohen IP Law Group P.C.; Michael N. Cohen

(57) ABSTRACT

Embodiments of the present invention relate to a topical anesthetizing apparatus that includes a first portion, second portion, numbing orb that is configured to be chilled, an open state, and a closed state. The first portion includes a first recess. The second portion comprises a second recess. In the closed state, the first recess and the second recess come together to form a sphere. Here, the numbing orb is selectively positioned within the sphere. In the open state, the first recess is positioned distal to the second recess and the numbing orb is selectively positioned within the first recess or the second recess. The first portion is hinge attached to the second portion. Here, the numbing orb is configured to be topically applied to the skin of a mammal to thereby topically anesthetize the skin.

13 Claims, 12 Drawing Sheets

TOPICAL ANESTHETIZING APPARATUS

BACKGROUND

The present disclosure relates generally to the field of anesthetizing apparatus, and more particularly to topical anesthetizing apparatus. Pain is a major limiting factor in many common procedures performed in the inpatient and ambulatory care settings. A very abbreviated list includes skin biopsy, fine needle aspiration biopsy, IV insertion, vaccination, injections (including injection of anesthetics), blood draws, central line placements, and finger and heal pricks for blood analysis (glucose measurement). Pharmacologic anesthesia is a primary method of pain reduction, but the delivery of local pharmacologic anesthesia usually requires a painful injection. Other methods of providing anesthesia include the application of cold temperatures through ice, liquid evaporation, or low temperature substances.

Skin can be numbed for a variety of reasons. For example, skin may be temporarily numbed to relieve pain caused by, for example, sunburn from overexposure to the sun's ultraviolet radiation, dermatitis caused by coming in contact with a substance that irritates or causes an allergic reaction, skin injuries that do not penetrate to the point that blood appears. Skin may also be temporarily numbed in anticipation of future pain that results from a medical procedure (e.g., receiving stiches to close a wound, receiving dermabrasion, etc.) as well as cosmetic procedures (e.g., ear piercing, tattooing, hair removal, waxing, and similar procedures.

DETAILED DESCRIPTION

Figure 1:
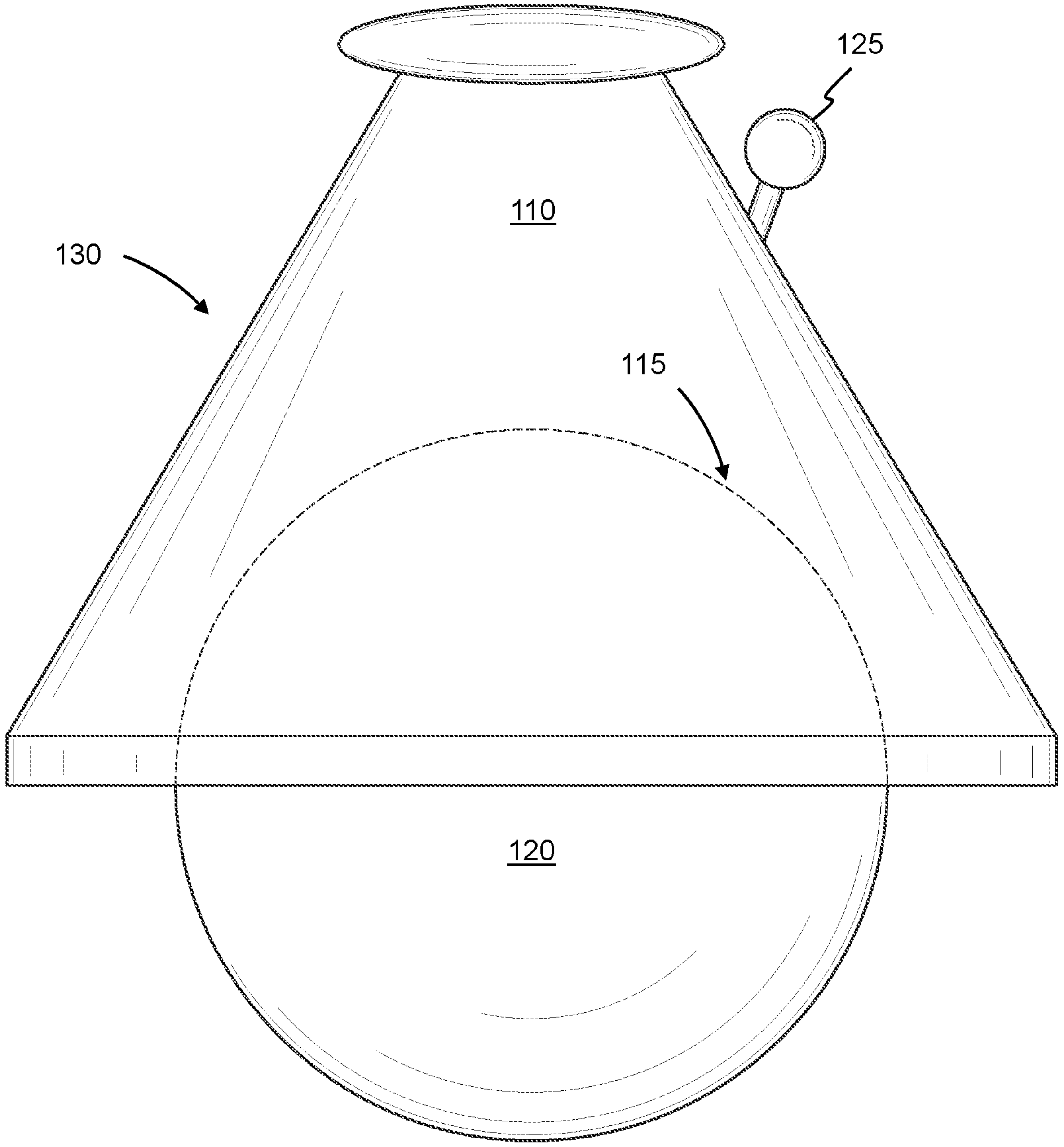
FIG. 1 depicts a side view of a first portion of a topical anesthetizing apparatus in an open state with a numbing orb positioned therein, according to other embodiments.
Figure 2:
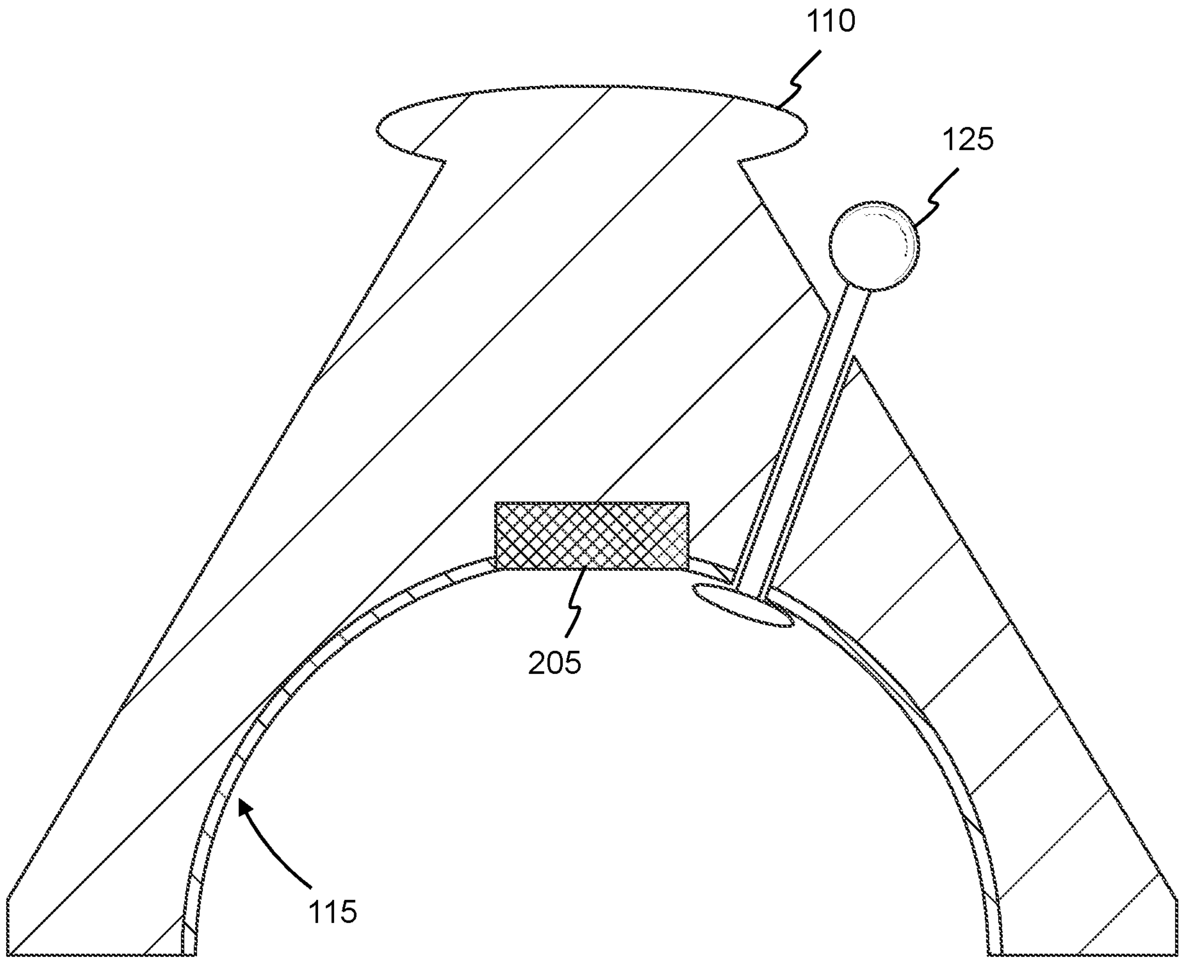
FIG. 2 depicts a side through view of the first portion, according to some embodiments.
Figure 3:
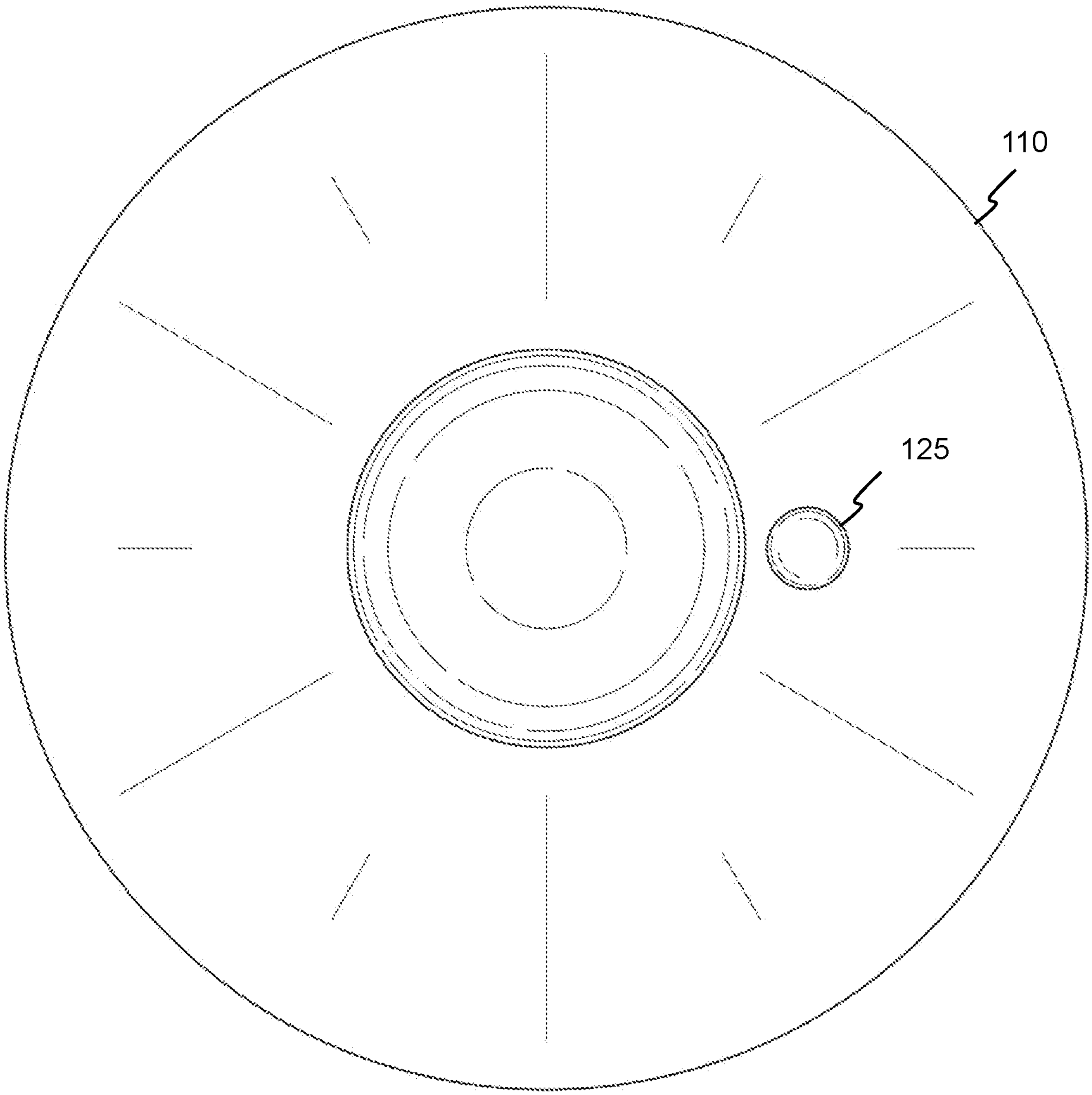
FIG. 3 depicts a top view of the first portion, according to certain embodiments.
Figure 4:
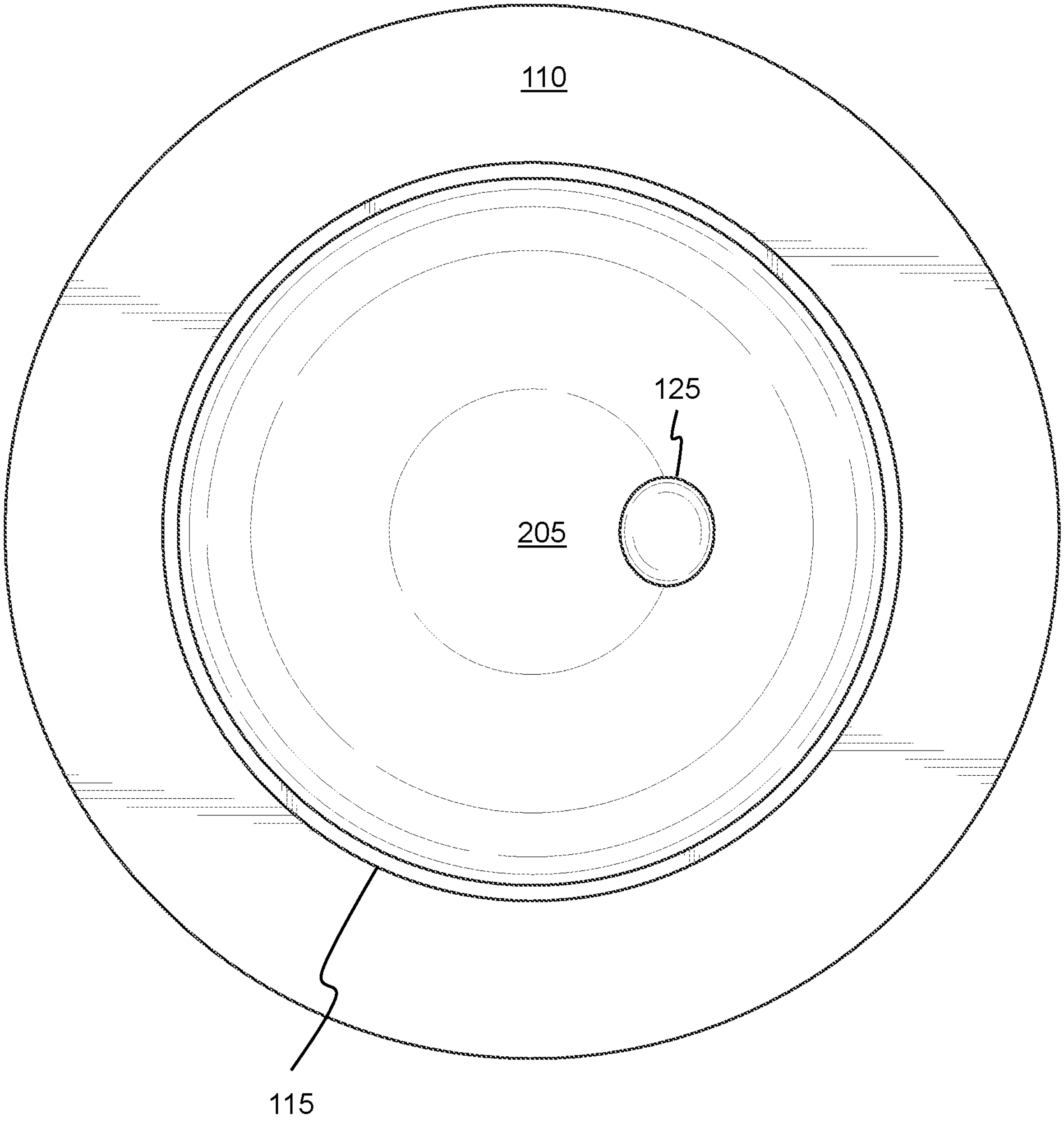
FIG. 4 depicts a bottom view of the first portion, according to yet still other embodiments.
Figure 5:
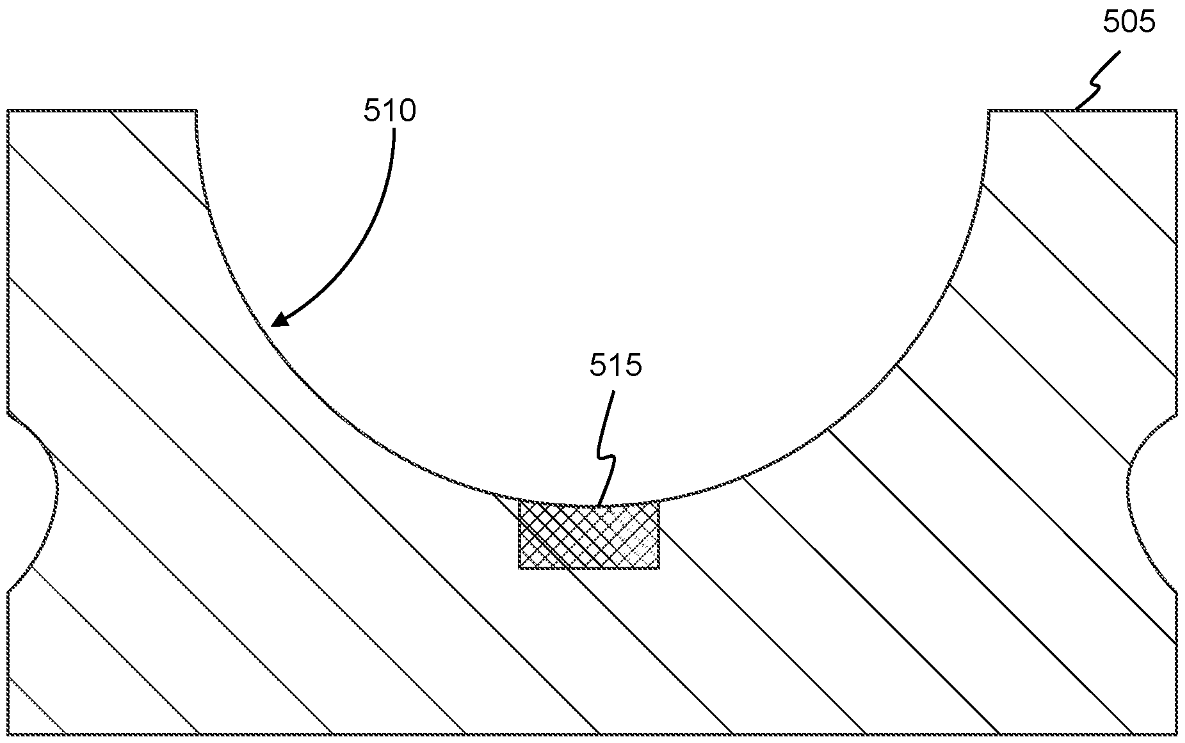
FIG. 5 depicts a side through view of a second portion of the topical anesthetizing apparatus, according to some embodiments.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Certain terminology may be employed in the following description for convenience rather than for any limiting purpose. For example, the terms "forward" and "rearward," "front" and "rear," "right" and "left," "upper" and "lower," and "top" and "bottom" designate directions in the drawings to which reference is made, with the terms "inward," "inner," "interior," or "inboard" and "outward," "outer," "exterior," or "outboard" referring, respectively, to directions toward and away from the center of the referenced element, the terms "radial" or "horizontal" and "axial" or "vertical" referring, respectively, to directions or planes which are perpendicular, in the case of radial or horizontal, or parallel, in the case of axial or vertical, to the longitudinal central axis of the referenced element, the terms "proximate" and "distal" referring, respectively, to positions or locations that are close or away from a point of reference, and the terms "downstream" and "upstream" referring, respectively, to directions in and opposite that of fluid flow. Terminology of similar import other than the words specifically mentioned above likewise is to be considered as being used for purposes of convenience rather than in any limiting sense.

In the figures, elements having an alphanumeric designation may be referenced herein collectively or in the alternative, as will be apparent from context, by the numeric portion of the designation only. Further, the constituent parts of various elements in the figures may be designated with separate reference numerals which shall be understood to refer to that constituent part of the element and not the element as a whole. General references, along with references to spaces, surfaces, dimensions, and extents, may be designated with arrows. Angles may be designated as "included" as measured relative to surfaces or axes of an element and as defining a space bounded internally within such element therebetween, or otherwise without such designation as being measured relative to surfaces or axes of an element and as defining a space bounded externally by or outside of such element therebetween. Generally, the measures of the angles stated are as determined relative to a common axis, which axis may be transposed in the figures for purposes of convenience in projecting the vertex of an angle defined between the axis and a surface which otherwise does not extend to the axis. The term "axis" may refer to a line or to a transverse plane through such line as will be apparent from context.

Skin can be numbed for a variety of reasons. For example, skin may be temporarily numbed to relieve pain caused by, for example, sunburn from overexposure to the sun's ultraviolet radiation, dermatitis caused by coming in contact with a substance that irritates or causes an allergic reaction, skin injuries that do not penetrate to the point that blood appears. Skin may also be temporarily numbed in anticipation of future pain that results from a medical procedure (e.g., receiving stiches to close a wound, receiving dermabrasion, etc.) as well as cosmetic procedures (e.g., ear piercing, tattooing, hair removal, waxing, and similar procedures.

Embodiments of the instant disclosure seek to provide a topical anesthetizing apparatus ("apparatus") that is configured to be topically used in anticipation of future pain that results from a medical procedure Other aspects of the instant disclosure seek to an apparatus that is reusable. Additional aspects of the present invention seek to provide an apparatus that is handheld and portable.

Turning now to the FIGS. FIGS. 1-6B depicts a first embodiment of a topical anesthetizing apparatus (hereinafter "apparatus") 600, according to some embodiments. The apparatus 600 includes a first portion 110, a second portion 505, and a numbing orb 120. The first portion 110 and the second portion 505 can be formed using polymers and/or metals. Although the first portion 110 is depicted as having an overall triangular structure and the second portion 505 is depicted as having an overall rectangular structure, either component can have an overall structure that is ovular and/or polygonal. To be sure, the overall structure should facilitate the overall handheld nature of the apparatus 600. The first portion 110 includes a first recess 115 and the second portion 505 includes a second recess 510.

The first recess 115 and the second recess 510 come together to form a sphere 635. The first recess 115 and/or the second recess 510 include a magnet (e.g., a magnet 205 and a magnet 515, respectively), which selectively secures the numbing orb 120. The first portion 115 (or the second portion 505) includes a traversing release button 125 positioned proximate to the magnet. The traversing release button 125 selectively dislodges the numbing orb 125 from the magnet when compressed. The numbing orb 125 can be formed in a variety of manners. For example, the numbing orb 125 can be a metallic structure that has a powder coating.

The numbing orb can also be a hollow polymeric structure (e.g., a numbing orb 620) that is at least partially filled with a liquid (e.g., a liquid filling 622). The polymer material is preferably food grade. The liquid filling can include, but is not limited to, water, hydroxyethyl cellulose, sodium polyacrylate, a polymer, a glycol, glycerin, and/or silica coated with vinyl. Here, the numbing orb 620 includes a metal tab 640 externally affixed thereto that allows the numbing orb 620 to be selectively positioned within the first recess 115 or the second recess 505. In some embodiments, the metal tab 640 is internally affixed to the numbing orb 620. For example, the portion of the numbing orb 620 around the metal tab 640 (e.g., a portion 650) can have a greater thickness compared to the rest of the circumference of the numbing orb 620.

Figure 6A:
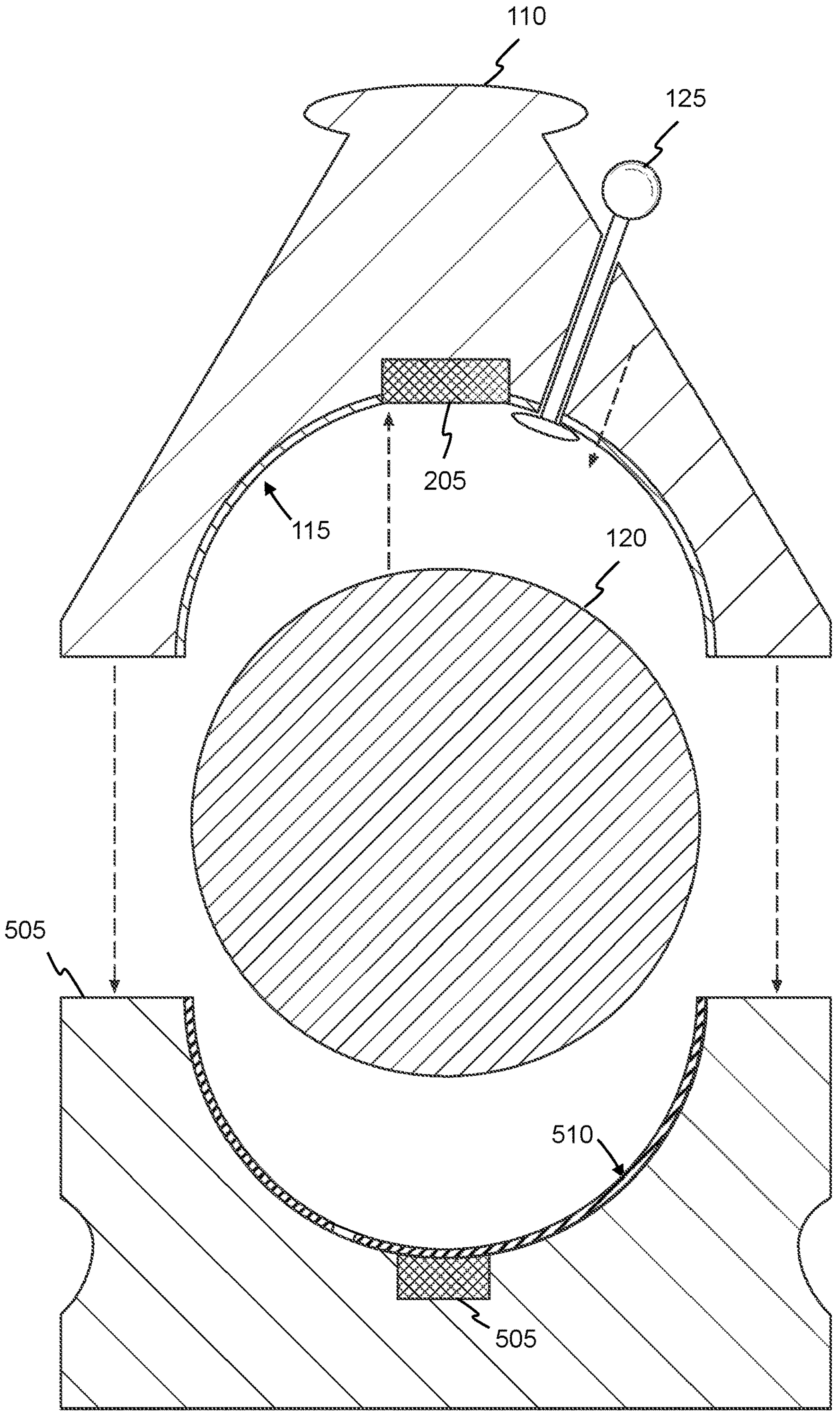
FIG. 6A depicts a side through view of the topical anesthetizing apparatus in the open state, according to other embodiments.
Figure 6B:
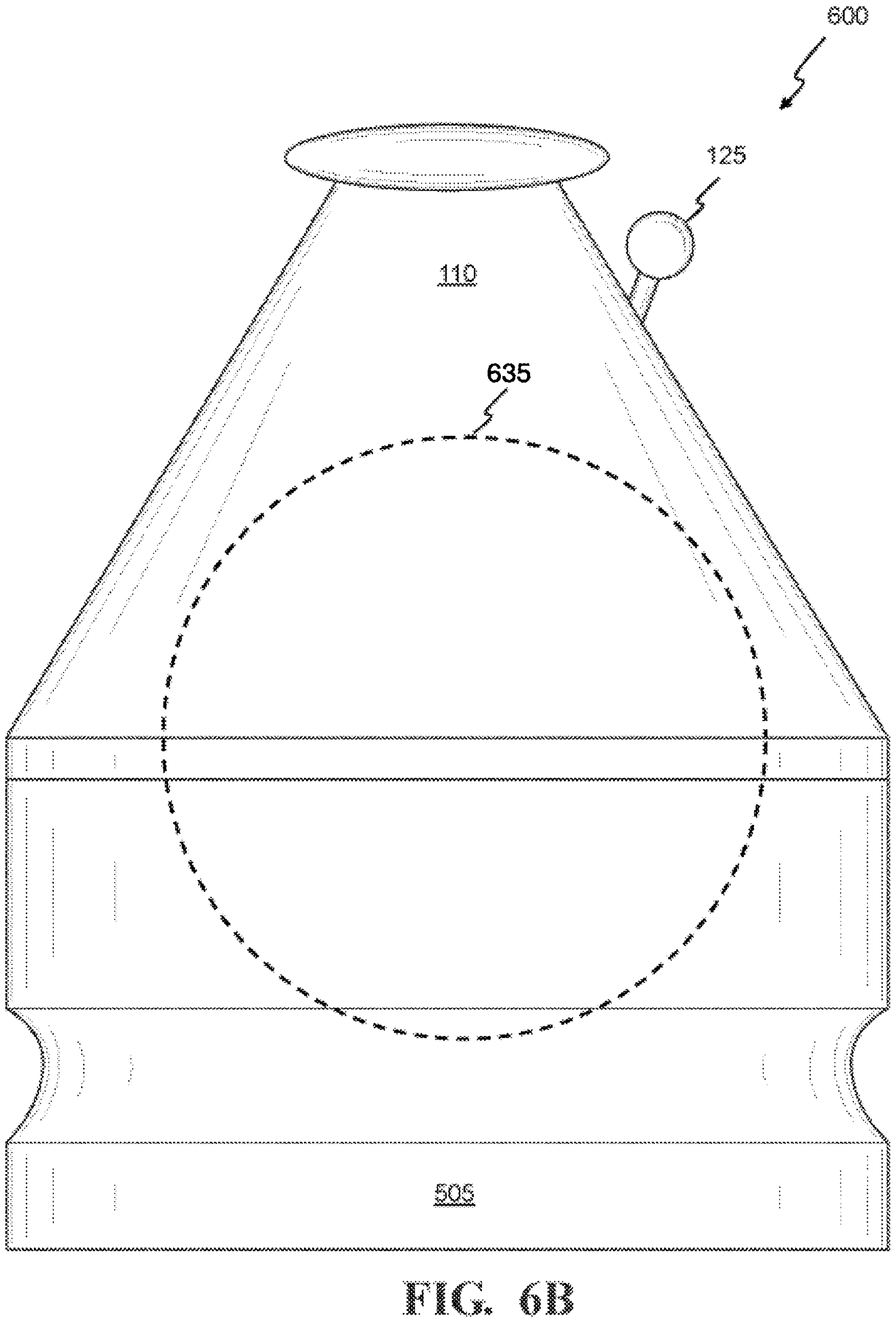
FIG. 6B depicts a side view of the anesthetizing apparatus in a closed state, according to some embodiments.
Figure 6C:
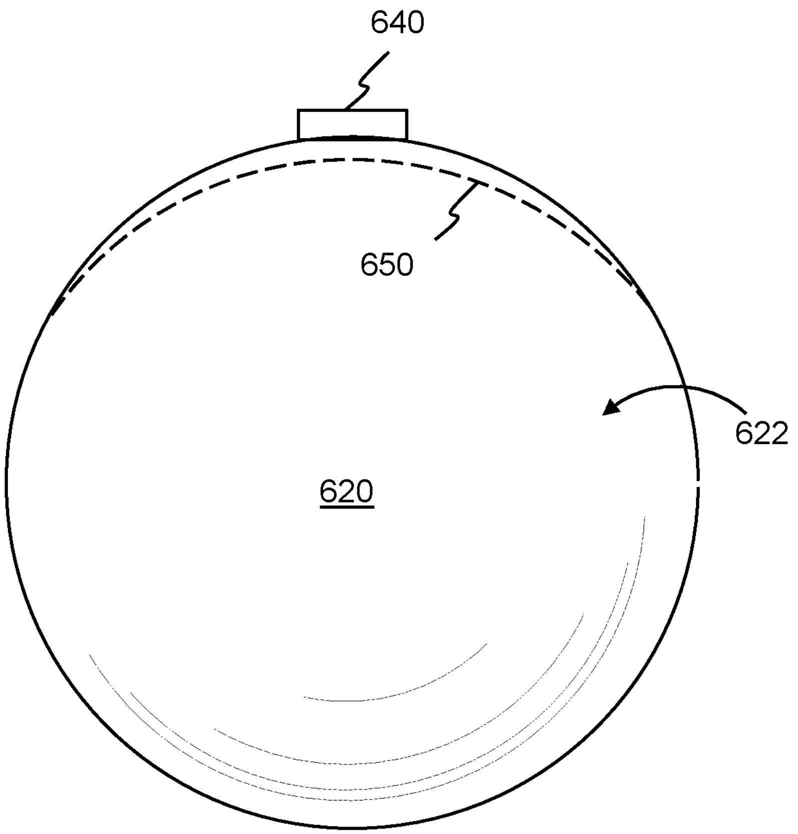
FIG. 6C depicts a side view of a numbing orb, according to other embodiments.
Figure 7:
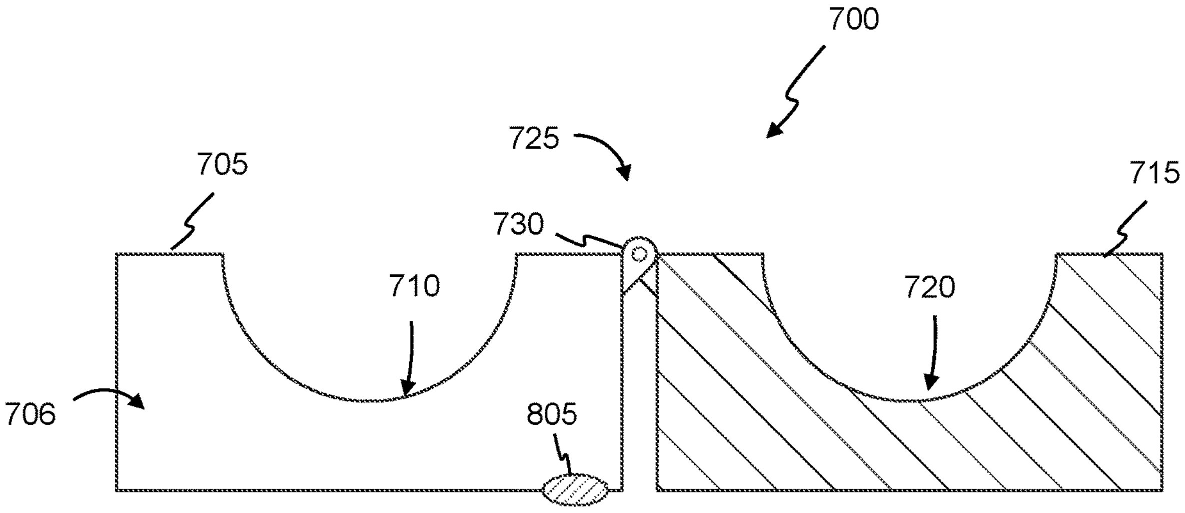
FIG. 7 depicts a side through view of a topical anesthetizing apparatus in an open state, according to certain embodiments.
Figure 8:
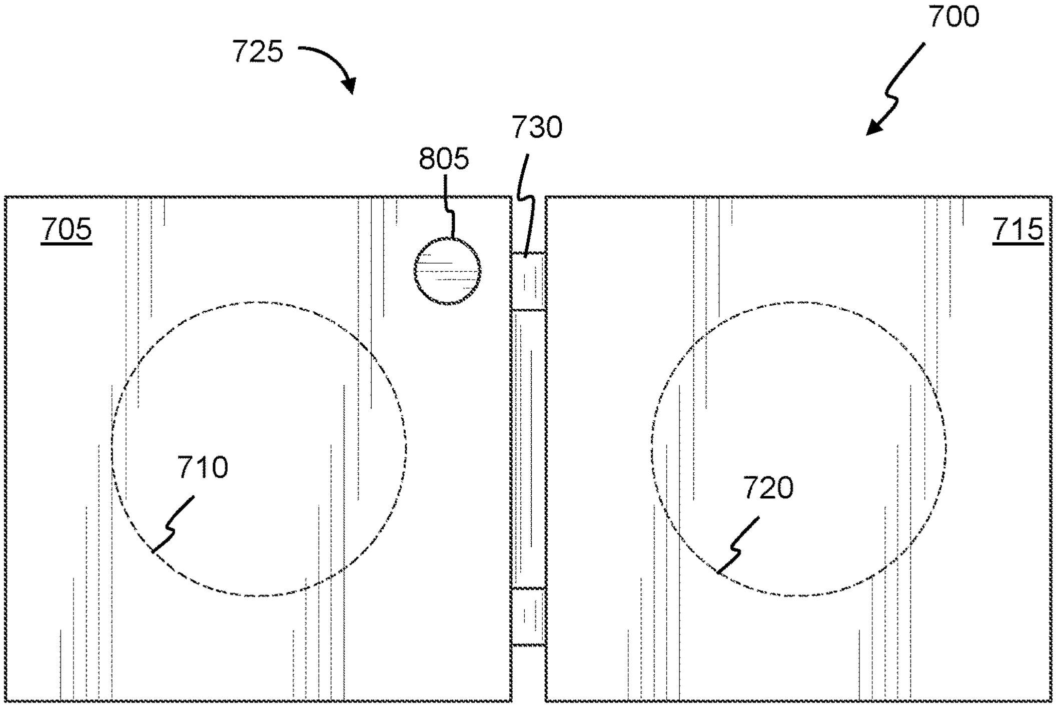
FIG. 8 depicts a bottom view of the topical anesthetizing apparatus in the open state, according to yet still other embodiments.
Figure 9:
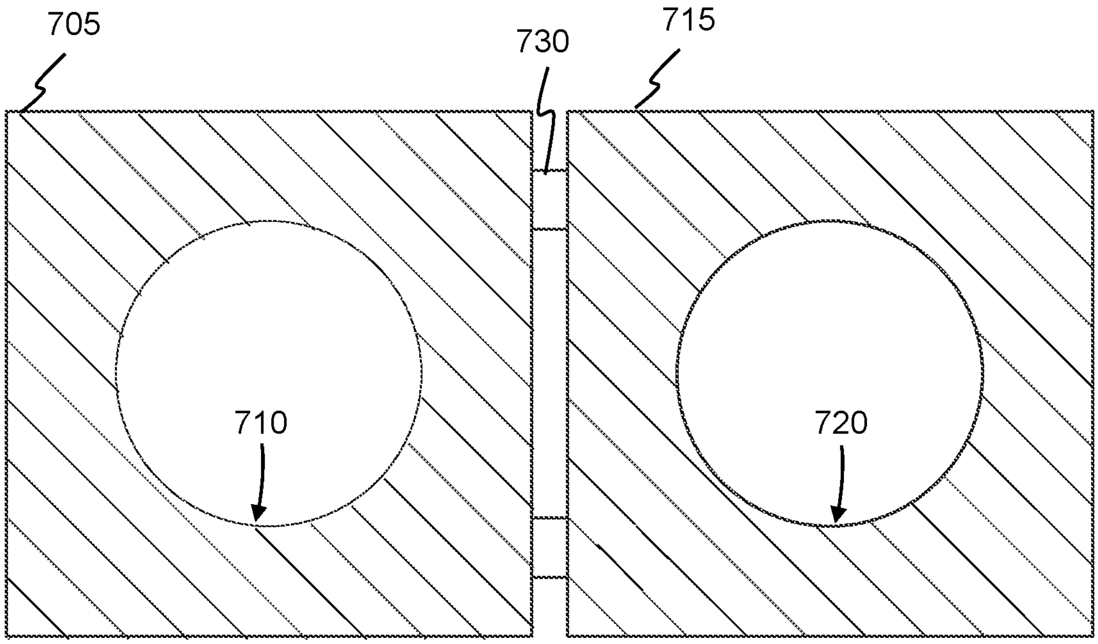
FIG. 9 depicts a top view of the topical anesthetizing apparatus in the open state, according to some embodiments.
Figure 10:
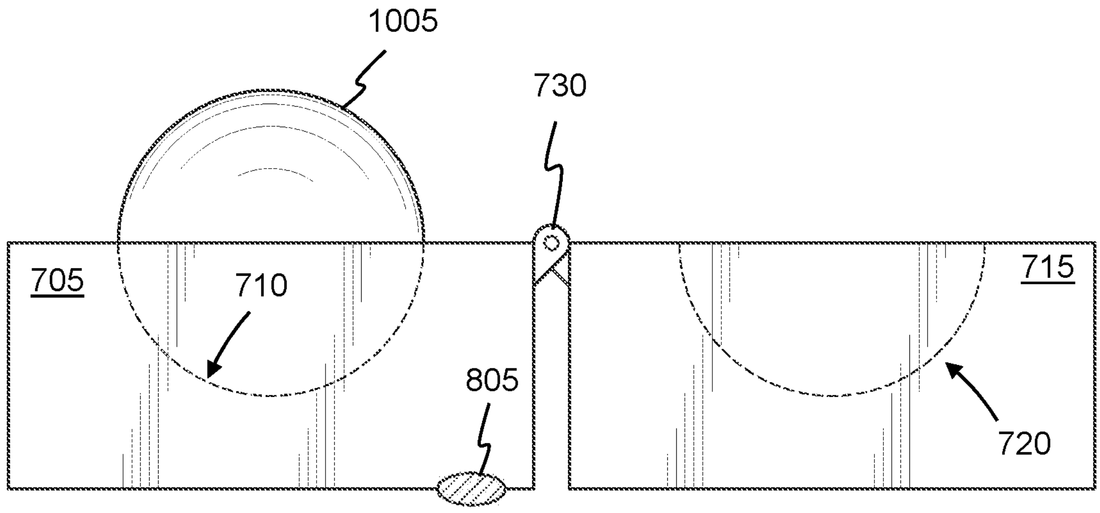
FIG. 10 depicts a side view of the topical anesthetizing apparatus in the open state, according to other embodiments.
Figure 11:
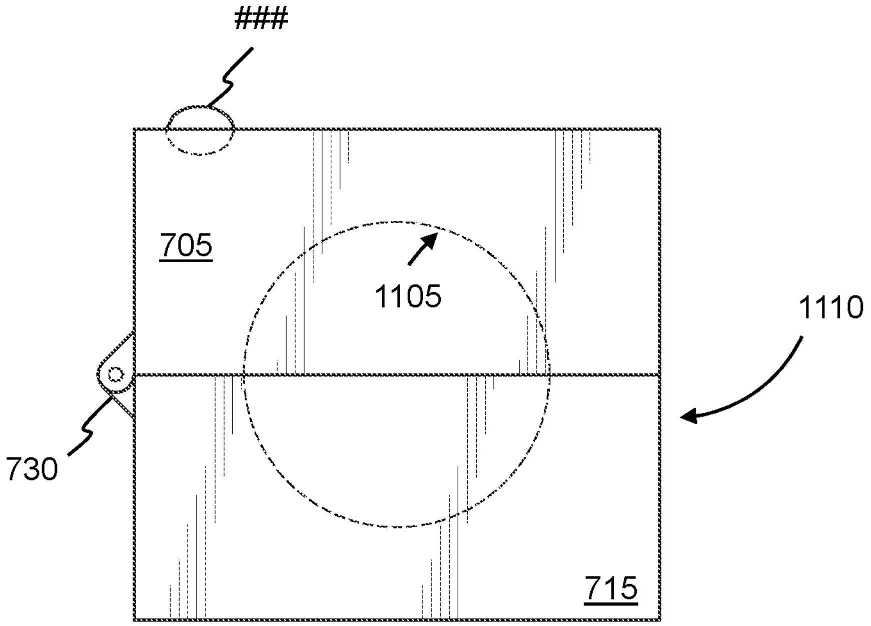
FIG. 11 depicts a side view of the topical anesthetizing apparatus in a closed state, according to certain embodiments.
Figure 12:
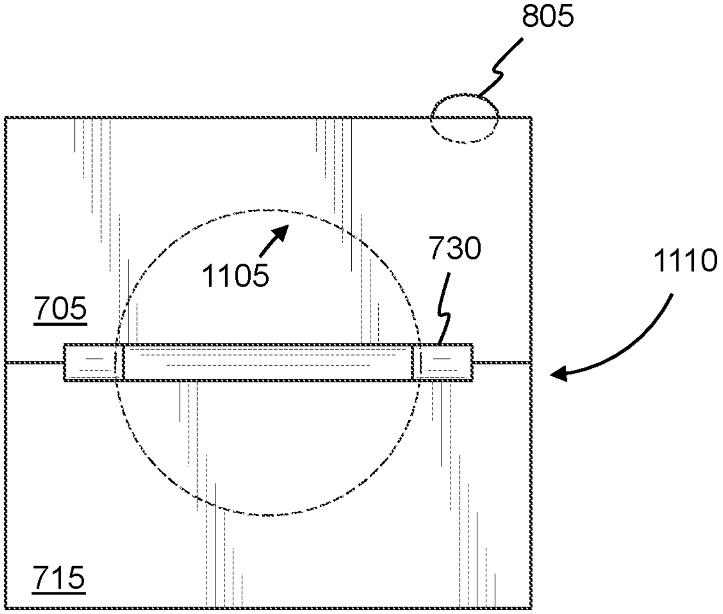
FIG. 12 depicts a rear view of the topical anesthetizing apparatus in the closed state, according to yet still other embodiments.
Figure 13:
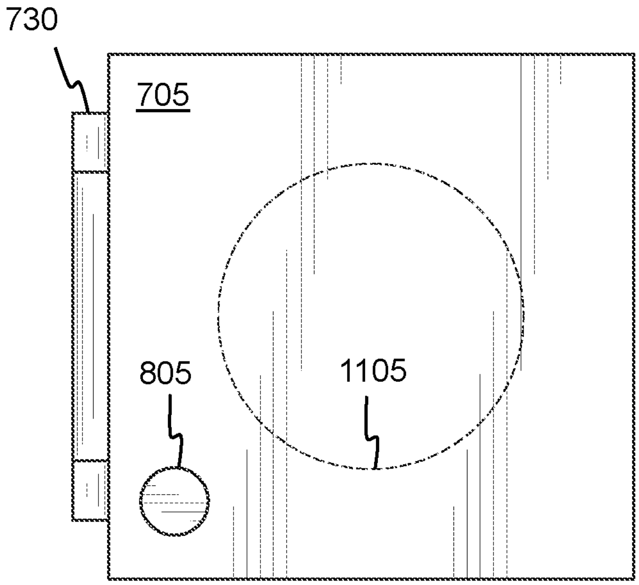
FIG. 13 depicts a top view of the topical anesthetizing apparatus in the closed state, according to some embodiments.

The apparatus 600 can be oriented in an open state 130 (e.g., depicted in FIG. 1) and a closed state 630 (e.g., depicted in FIG. 6B). In the closed state 630, the numbing orb 125 is selectively positioned within the sphere 635. The apparatus 100 is configured to temporarily numb skin in preparation of future pain. In the open state 130, the first recess 115 is positioned distal to (i.e., away from) the second recess 505. Here, the numbing orb 120 is selectively positioned within the first recess 115 or the second recess 505 and is configured to be topically applied to the skin of a mammal to thereby anesthetize the skin.

FIGS. 7-13 depict a topical anesthetizing apparatus (hereinafter "apparatus") 700, according to some embodiments. The apparatus 700 can share one or more features, components, and/or functionalities with apparatus 600. The apparatus 700 includes a first portion 705, a second portion 715, and a numbing orb 1005. The numbing orb 1005 can share one or more features, components, and/or functionalities with the numbing orb 125. The first portion 705 includes a first recess 710 and the second portion 715 includes a second recess 720. The first recess 710 and the second recess 720 come together to form a sphere 1105.

Here, the first portion 705 is hinge attached (e.g., via a hinge 730) to the second portion 715. The first portion 705 and/or the second portion 715 can include a void 706 internally positioned therein and an access port 805 externally positioned thereon. The access port 805 is functionally coupled to the void 706. The void 706 is configured to receive a liquid via the access port. Here, applicable liquids include, but are not limited to, water. The access port 805 preferably includes a food-grade tab that acts as a stopper. Here, the apparatus 700 can be filled with water and placed in a freezer to thereby freeze the water and chill the numbing orb 1005. FIGS. 7-10 depicts the apparatus 700 in an open state 725, which allows the apparatus 700 to operate in a similar fashion compared to the apparatus 600 in the open state 130. FIGS. 11-15 depicts the apparatus 700 in a closed state 725, which allows the apparatus 700 to operate in a similar fashion compared to the apparatus 600 in the closed state 630.

The apparatus 600 or the apparatus 700 (hereinafter "the apparatus") is preferably used in a method to topically anesthetize the skin of a mammal. The method includes chilling the numbing orb of the topical anesthetizing apparatus. Here, chilling the numbing orb can include placing the numbing orb, the first portion, and/or the second portion in a freezer (e.g., 5-30 minutes). Water can be added to the first portion and/or the second portion via the access port attached thereto prior to chilling the numbing orb. While the apparatus is in the open state, the chilled numbing orb is applied to skin (i.e., at a predetermined location that will receive the future topical pain) to topically anesthetize the skin. Preferably, the skin is dried (i.e., void of visible moisture) prior to applying the chilled numbing orb to the skin. The skin location that received the chilled numbing orb is ready to receive a needle injection (e.g., for insulin or other injectable medication). Subsequently, the numbing orb can be dislodged from the magnet positioned in the first portion or the second portion via the traversing release button, the release button is positioned proximate to the magnet. Components of the apparatus can be cleaned with soap and water to maintain sanitary conditions.

Based on the foregoing, a topical anesthetizing apparatus has been disclosed in accordance with the present invention. However, numerous modifications and substitutions can be made without deviating from the scope of the present invention. Therefore, the present invention has been disclosed by way of example and not limitation.

What is claimed is:

1. A topical anesthetizing apparatus, comprising:

a first portion;

a second portion;

an internal void within the first portion or the second portion and a corresponding access port functionally coupled to the internal void, the internal void configured to receive a liquid via the access port and being entirely sealed when the access port is closed;

a numbing orb that is configured to be chilled;

an open state;
a closed state;
wherein
the first portion comprises a first recess;
the second portion comprises a second recess;
in the closed state,
the first recess and the second recess come together to form a sphere;
the numbing orb is selectively positioned within the sphere;
in the open state,
the first recess is positioned distal to the second recess;
the numbing orb is selectively positioned within the first recess or the second recess;
and
configured to be topically applied to the skin of a mammal to topically anesthetize the skin.

2. The topical anesthetizing apparatus of claim 1, wherein the first portion is hinge attached to the second portion.

3. The topical anesthetizing apparatus of claim 1, wherein one or more of the first recess and the second recess comprise a magnet; and
the magnet selectively secures the numbing orb.

4. The topical anesthetizing apparatus of claim 3, wherein the numbing orb
is a hollow polymeric structure;
comprises a liquid filing; and
the liquid filling comprises one or more of water, hydroxy ethyl cellulose,
sodium polyacrylate, a polymer, a glycol, glycerin, and silica coated with vinyl.

5. The topical anesthetizing apparatus of claim 3, wherein the first portion or the second portion comprises a traversing release button positioned proximate to the magnet; and
the traversing release button selectively dislodges the numbing orb from the magnet when compressed.

6. A method to anesthetize the skin of a mammal comprising:
adding water to the first portion and/or the second portion via the access port and then chilling the numbing orb of the topical anesthetizing apparatus of claim 1; and
while the topical anesthetizing apparatus is in the open state, applying the chilled numbing orb to skin of a mammal to thereby topically anesthetize the skin.

7. The method of claim 6, wherein
chilling the numbing orb comprises placing one or more of the numbing orb, the first portion, and the second portion in a freezer for 5-30 minutes.

8. The method of claim 6, further comprising:
dislodging the numbing orb from a magnet positioned in the first portion or the second portion via a traversing release button, the release button is positioned proximate to the magnet.

9. A topical anesthetizing apparatus, comprising:
a first portion;
a second portion;
a numbing orb that is configured to be chilled;
an open state;
a closed state;
wherein
the first portion comprises a first recess;
the second portion comprises a second recess;
in the closed state,
the first recess and the second recess come together to form a sphere;
the numbing orb is selectively positioned within the sphere;
in the open state,
the first recess is positioned distal to the second recess;
the numbing orb is selectively positioned within the first recess or the second recess;
and
configured to be topically applied to the skin of a mammal to topically anesthetize the skin;
wherein the numbing orb is a metallic structure and comprises a powder coating.

10. A topical anesthetizing apparatus, comprising:
a first portion;
a second portion;
a numbing orb that is configured to be chilled;
an open state;
a closed state;
wherein
the first portion comprises a first recess;
the second portion comprises a second recess;
in the closed state,
the first recess and the second recess come together to form a sphere;
the numbing orb is selectively positioned within the sphere;
in the open state,
the first recess is positioned distal to the second recess;
the numbing orb is selectively positioned within the first recess or the second recess;
and
configured to be topically applied to the skin of a mammal to topically anesthetize the skin;
wherein the numbing orb comprises a metal tab externally affixed that allows the numbing orb to be selectively positioned within the first recess or the second recess.

11. The topical anesthetizing apparatus of claim 10, wherein
one or more of the first recess and the second recess comprise a magnet; and
the magnet selectively secures the numbing orb.

12. The topical anesthetizing apparatus of claim 11, wherein
the first portion or the second portion comprises a traversing release button positioned proximate to the magnet; and
the traversing release button selectively dislodges the numbing orb from the magnet when compressed.

13. The topical anesthetizing apparatus of claim 10, wherein
the numbing orb is a hollow polymeric structure;
comprises a liquid filling; and
the liquid filling comprises one or more of water, hydroxy ethyl cellulose, sodium polyacrylate, a polymer, a glycol, glycerin, and silica coated with vinyl.

* * * * *